United States Patent [19]

Blass et al.

[11] 4,406,751
[45] Sep. 27, 1983

[54] ELECTROCHEMICAL DETERMINATION OF ORTHOPHOSPHORIC MONOESTER PHOSPHOHYDROLASE ACTIVITY (EC 3.1.3.1 AND EC 3.1.3.2: ALKALINE AND ACID PHOSPHATASES)

[76] Inventors: Karl G. Blass, 148 Cardinal Crescent, Regina, Saskatchewan, Canada; Chung-Shun Ho, 2H, Shek Kip Mei St., 2/F, Flt A, Shamshuipo, Kln, Hong Kong

[21] Appl. No.: 333,573

[22] Filed: Aug. 11, 1982

[51] Int. Cl.[3] .................. G01N 27/56; C12Q 1/42
[52] U.S. Cl. .................................. 204/1 T; 435/21
[58] Field of Search ............... 204/1 E; 435/21, 19

[56] References Cited

U.S. PATENT DOCUMENTS 3,896,008  7/1975  Keyes ........................... 204/1 T
4,059,490  11/1977  Axcell et al. ............... 204/1 T X Primary Examiner—G. L. Kaplan
Attorney, Agent, or Firm—Stanley G. Ade

[57] ABSTRACT

A method is disclosed for the measurement of acid and alkaline phosphatase activity, whereby an aromatic phosphate ester substrate containing a nitro group is reacted with acid or alkaline phosphatase under appropriate reaction conditions and the hydrolytic process is monitored at electrodes which measure the current produced by the reduction of the nitro groups of the product and/or substrate. Alternatively, an aromatic phosphate ester substrate containing an amino group is reacted with acid or alkaline phosphatase under appropriate reaction conditions with the hydrolytic process being monitored at solid electrodes which measure the current produced by the oxidation of the amino groups of the product and/or substrate.

2 Claims, 10 Drawing Figures

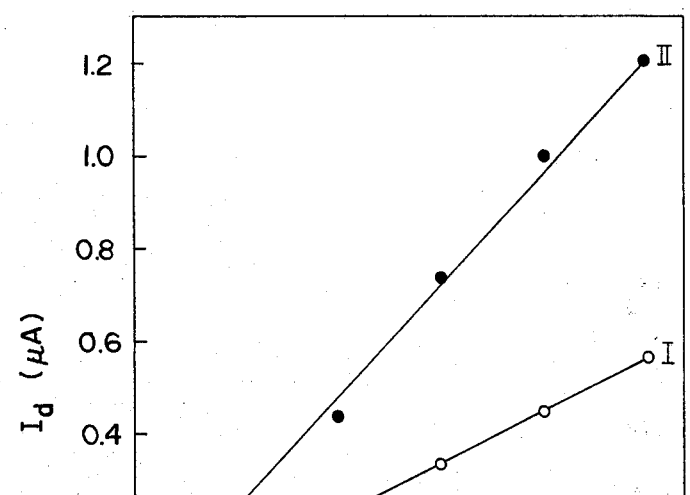

ELECTROCHEMICAL DETERMINATION OF ORTHOPHOSPHORIC MONOESTER PHOSPHOHYDROLASE ACTIVITY (EC 3.1.3.1 AND EC 3.1.3.2: ALKALINE AND ACID PHOSPHATASES)

BACKGROUND OF THE INVENTION

This invention relates to a new and useful electrochemical process for the detection and measurement of orthophosphoric monoester phosphohydrolase activity (EC3.1.3.1 and EC3.1.3.2). These enzymes are commonly known as alkaline and acid phosphatase, depending upon whether they prefer reaction conditions of about pH 10.0 or pH 5.0, respectively. The phosphatases have a low substrate specificity and the general chemical reaction involves the hydrolysis of a monophosphoric ester substrate to its corresponding alcohol and phosphate ion. For example, alkaline phosphatase (ALP) hydrolyzes p-nitrophenyl phosphate (PNPP) to p-nitrophenol (PNP) and phosphate ion (Ref. 1). The chemical reaction is depicted as follows:

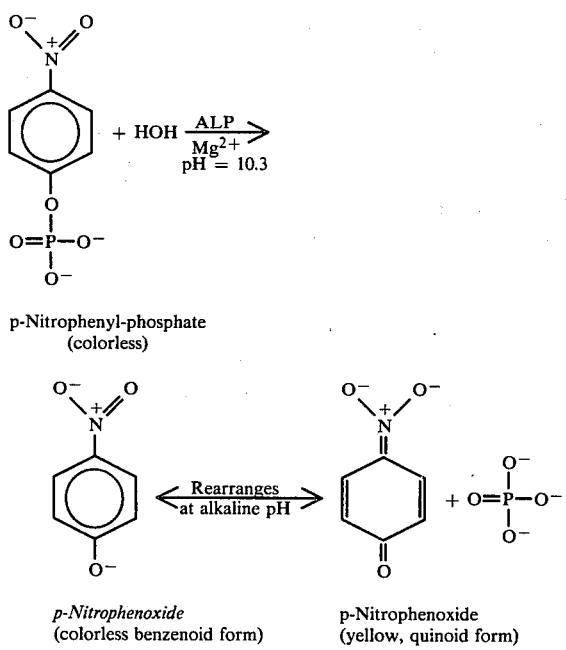

In the presence of excess substrate, under appropriate reaction conditions, the rate limiting factor is the concentration and activity of the ALP. A similar hydrolysis reaction occurs under acidic conditions in the presence of acid phosphatase (ACP).

The measurement of serum ALP activity is of primary importance for the diagnosis of two groups of conditions: hepatobiliary disease, and bone disease associated with increased osteoblastic activity (Refs. 2,4). Moderate elevations of serum ALP have been reported for parenchymal liver disease e.g. infectious hepatitis, infectious mononucleosis, portal cirrhosis, and the like. Elevated serum ALP has also been reported for the following bone associated diseases: Paget's disease, Fanconi syndrome, osteomalacia, rickets, hyperparathyroidism, and bone cancer (Refs. 2,4).

Similar to ALP, ACP is widely distributed throughout the body tissues. However, the major diagnostic application of serum ACP measurement is for males with prostatic cancer with metastases (Refs. 3,5). More specific testing of the prostatic ACP fraction may be accomplished by employing a tartrate inhibition test procedure (Ref. 3).

SUMMARY OF THE INVENTION

The process described herein may be employed to measure acid and alkaline phosphatase activity. An aromatic phosphate ester substrate containing a nitro group is reacted with acid or alkaline phosphatase under appropriated reaction conditions and the hydrolytic process is monitored at electrodes which measure the current produced by the reduction of the nitro groups of the product and/or substrate. The process may be adapted to measure phosphatase activities in: animal body fluids or tissues; plants; and, microorganisms. The process, with or without modification, may be adapted to polarographic and other electrochemical apparatus currently available, or specific analyzers may more economically be built to monitor the electrochemical reactivity of nitro groups of the substrate and/or product.

The electrochemical detection procedure described herein for the measurement of alkaline and acid phosphatase activity is highly specific and sensitive. Chromogenic and turbidimetric interferences are eliminated due to the nature of the detection system.

In accordance with the invention there is provided a process for the measurement of phosphatase activity in serum, other fluids or tissues brought into solution; whereby, the sample is allowed to react with an aromatic phosphate ester substrate containing a nitro group, with the hydrolysis process being monitored at electrodes. The phosphatase activity is established by conventional kinetic techniques, end-point techniques, and the like.

In the analyses included herein by way of examples, the following chemicals were obtained from Sigma Chemical Co., St. Louis, Missouri: ALP enzyme (from chicken intestine), p-nitrophenylphosphate hexahydrate (PNPP), and sodium nitrite. Normal human pooled serum was obtained from the Regina General Hospital, Regina, Saskatchewan, Canada. Certified A.C.S. grade ethylenediaminetetraacetic acid (EDTA), p-nitrophenol (PNP), sodium chloride, and sodium hydroxide were obtained from Fisher Scientific Co., Fair Lawn, N.J. Reagent grade magnesium chloride hexahydrate and sodium bicarbonate were purchased from J. T. Baker Chemical Co., Phillipsburg, N.J. The activating buffer, 2-amino-2-methyl-1-propanol (AMP) was obtained from Eastman Kodak Co., Rochester, N.Y. Concentrated hydrochloric acid was supplied by Canadian Industries Ltd., St. Boniface, Manitoba, Canada. However, other sources of chemicals can of course be used.

For polarographic analyses, a Sargent Model XVI polarograph from Sargent-Welch Scientific Co., Toronto, Ontario, Canada, and a Model 170 Electrochemistry System from Princeton Applied Research, Princeton, N.J., were employed. Titration vessels (polarography cells), saturated calomel electrodes, and related accessories were from Brinkmann Instruments, Rexdale, Ontario, Canada. Triple distilled mercury was supplied by Engelhard Industries, Toronto, Ontario, Canada. Nitrogen gas (99.9% purity) from Canadian Liquid Air Ltd., Regina, Saskatchewan, Canada, was used to displace dissolved oxygen in the test solutions throughout this project. A constant temperature water bath was maintained by either a Thermomix-148 water pump from B. Braun, Melsungen AG, West Germany, or a Haake circulator from Fisher Scientific Co., Fair Lawn, N.J. A Gilford automatic dispenser was obtained from the Gilford Instrument Laboratory Inc., Oberlin, Ohio. The above instrumentation is listed for reference purposes only. Other instrumentation can of course be employed.

With the foregoing in view, and other advantages as will become apparent to those skilled in the art to which this invention relates as this specification proceeds, the invention is herein described by reference to the accompanying drawings forming a part thereof, which includes a description of a typical embodiment of the principles of the present invention in which:

DESCRIPTION OF THE DRAWINGS

FIG. 6 contains plots of diffusion current versus p-nitrophenylphosphate concentration in AMP buffer at pH 12.0 for nitro group reduction waves I and II, at $E_{\frac{1}{2}}$ values of $-0.25$ and $-0.76$ volts, respectively.

FIG. 7 contains plots of diffusion current versus p-nitrophenol in AMP buffer at pH 12.0 for nitro group reduction waves I and II, at $E_{\frac{1}{2}}$ values of $-0.35$ and $-0.85$ volts, respectively.

In the drawings like characters of reference indicate corresponding parts in the different figures.

DETAILED DESCRIPTION

Figure 1:
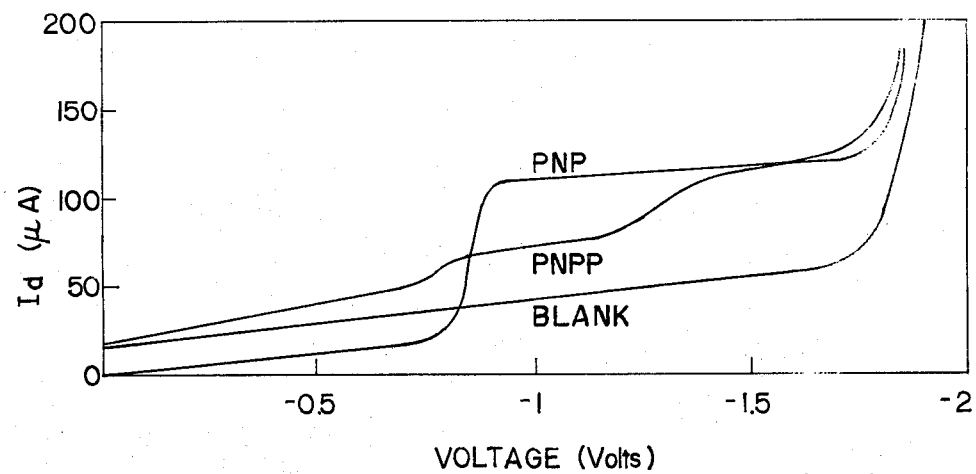
FIG. 1 contains plots of diffusion current versus voltage for a buffer blank solution, a buffer solution containing p-nitrophenylphosphate, and a buffer solution containing p-nitrophenol.

Proceeding therefore to describe the invention in detail, the following methods were used in preparing the necessary standards:

Polarographic Reduction of PNPP and PNP at Varied pH.

A 7.5 mM stock solution of PNPP was prepared by adding 0.06959 g of PNPP to a 25-ml volumetric flask which was filled to volume with distilled water. A supporting electrolyte medium was prepared by adding 1.050 g of anhydrous sodium carbonate, 0.05088 g of magnesium chloride hexahydrate, and 2.250 g of sodium chloride to a beaker containing 225 ml of distilled water. The solution was adjusted to pH 8.50 with 0.1 M sodium hydroxide, and transferred to a 250-ml volumetric flask which was filled to volume with distilled water.

Polarographic analyses were performed with a Sargent Model XVI Polarograph. A dropping mercury electrode (DME) was employed as the working electrode. A saturated calomel electrode was employed as the reference electrode. Analyses were performed in a water-jacketed polarography cell maintained at 25° C. Twenty-five milliliters of supporting electrolyte medium was transferred to the polarographic cell. The solution was deaerated for 10 min prior to polarographic analysis. The above procedure was similarly performed in duplicate. A typical supporting electrolyte polarogram (Blank) is presented in FIG. 1.

A Gilford automatic dispenser was employed to dispense reagent solutions. A PNPP test solution was prepared by dispensing 0.1 ml of PNPP stock solution into a 25-ml volumetric flask which was filled to volume with supporting electrolyte medium. Polarographic analysis was performed as previously described. The above procedure was similarly performed in duplicate. Half-wave potentials ($E_{\frac{1}{2}}$) and diffusion currents ($I_d$) were calculated from the polarograms by the "box technique" (Ref. 6).

A series of supporting electrolyte media were similarly prepared as described above, however, increasing amounts of 0.1 M sodium hydroxide were added to produce solutions of pH 9.00, 9.25, 9.50, 9.75, 10.00, 10.25, and 10.50. Corresponding PNPP test solutions were similarly prepared as previously described at pH 9.00, 9.25, 9.50, 9.75, 10.00, 10.25, and 10.50. Polarographic analysis of blank and test solutions were performed as previously described. Average $E_{\frac{1}{2}}$ and $I_d$ values have been calculated for each of the duplicate test solutions (see Table 1).

A 7.5 mM stock solution of PNP was prepared by adding 0.10435 g of PNP to a 100-ml volumetric flask which was filled to volume with distilled water. A PNP test solution was prepared by dispensing 0.1 ml of PNP stock solution into a 25-ml volumetric flask which was filled to volume with pH 8.50 supporting electrolyte medium. Polarographic analysis was performed as previously described. PNP test solutions were similarly prepared and analyzed using supporting electrolyte media of pH 9.00, 9.25, 9.50, 9.75, 10.00, 10.25, and 10.50. Average $E_{\frac{1}{2}}$ and $I_d$ values have been calculated for each of the duplicate test solutions (see Table 2).

Characteristic polarograms of a supporting electrolyte medium (Blank), a PNPP test solution, and a PNP test solution, each at pH 10.00, are depicted in FIG. 1.

TABLE 1

| | Polarographic reduction of PNPP at varied pH | | | |
|---|---|---|---|---|
| | Wave I | | Wave II | |
| pH | $E_{\frac{1}{2}}$ (volts)* | $I_d$ (μA)* | $E_{\frac{1}{2}}$ (volts)* | $I_d$ (μA)* |
| 8.50 | −0.773 | 0.080 | −1.307 | 0.140 |
| 9.00 | −0.783 | 0.080 | −1.305 | 0.142 |
| 9.25 | −0.790 | 0.084 | −1.307 | 0.144 |

TABLE 1-continued

Polarographic reduction of PNPP at varied pH

| pH | Wave I $E_{\frac{1}{2}}$ (volts)* | $I_d$ (μA)* | Wave II $E_{\frac{1}{2}}$ (volts)* | $I_d$ (μA)* |
|---|---|---|---|---|
| 9.50 | −0.783 | 0.088 | −1.302 | 0.150 |
| 9.75 | −0.779 | 0.086 | −1.304 | 0.142 |
| 10.00 | −0.785 | 0.080 | −1.303 | 0.140 |
| 10.25 | −0.792 | 0.084 | −1.306 | 0.140 |
| 10.50 | −0.782 | 0.084 | −1.300 | 0.140 |

*Each value reported represents an average of duplicate test results.

TABLE 2

Polarographic reduction of PNP at varied pH

| pH | Wave I $E_{\frac{1}{2}}$ (volts)* | $I_d$ (μA)* |
|---|---|---|
| 8.50 | −0.740 | 0.609 |
| 9.00 | −0.772 | 0.606 |
| 9.25 | −0.800 | 0.582 |
| 9.50 | −0.817 | 0.555 |
| 9.75 | −0.838 | 0.552 |
| 10.00 | −0.849 | 0.540 |
| 10.25 | −0.865 | 0.546 |
| 10.50 | −0.879 | 0.540 |

*Each value reported represents an average of duplicate test results.

Quantitation of PNPP and PNP

Figure 2:
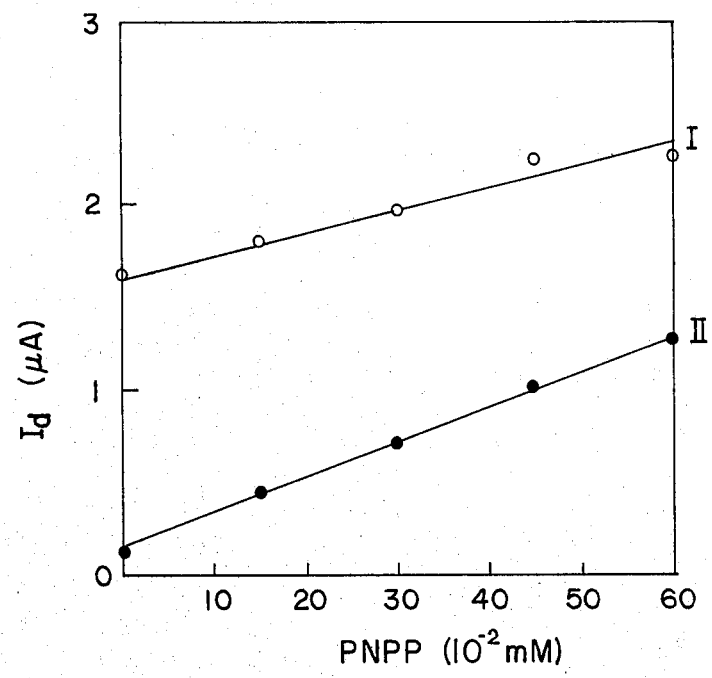
FIG. 2 contains plots of diffusion current versus p-nitrophenylphosphate concentration at pH 10.0 for nitro group reduction waves I and II, at $E_{\frac{1}{2}}$ values of $-0.82$ and $-1.28$ volts, respectively.

Stock solutions of PNPP and PNP were prepared as described under the DETAILED DESCRIPTION. A series of PNPP standards was prepared by pipetting 0, 0.5, 1.0, 1.5 and 2.0 ml of PNPP stock solution into five 25-ml volumetric flasks. A 0.3 ml volume of PNP stock solution was added to each flask. The volumetric flasks were filled to volume with pH 10.00 supporting electrolyte medium. This produced standard solutions containing 0, $15 \times 10^{-2}$, $30 \times 10^{-2}$, $45 \times 10^{-2}$, and $60 \times 10^{-2}$ mM of PNPP. The PNP concentration in each flask was $9 \times 10^{-2}$ mM. Polarographic analysis and subsequent measurements of $E_{\frac{1}{2}}$ and $I_d$ were performed as described under the DETAILED DESCRIPTION. Two polarographic reduction waves were observed at approximately $E_{\frac{1}{2}}$ values of −0.82 volts and −1.28 volts for waves I and II, respectively. The $I_d$ values for waves I and II were each plotted versus PNPP concentration (see Table 3 and FIG. 2).

Figure 3:
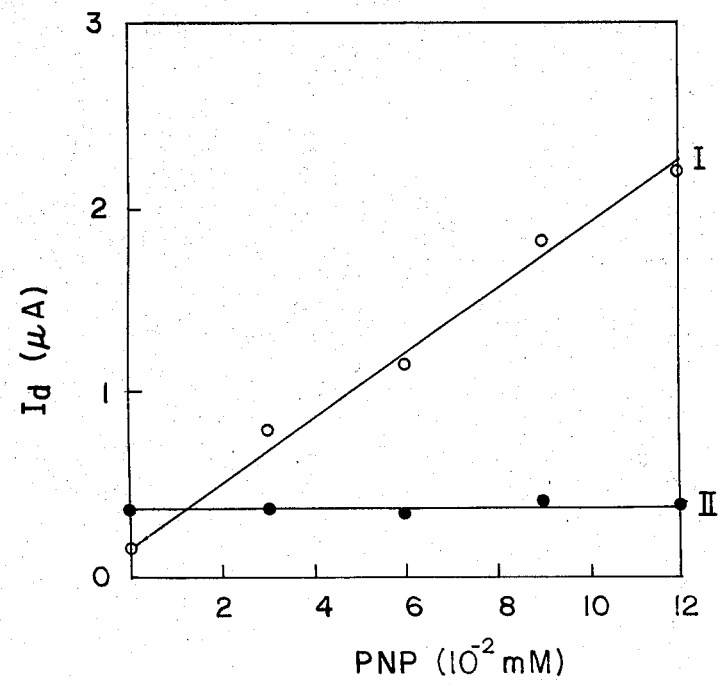
FIG. 3 contains plots of diffusion current versus p-nitrophenol concentration in the presence of $15 \times 10^{-2}$ mM p-nitrophenylphosphate at pH 10.0. Nitro group reduction waves I and II were at $-0.83$ and $-1.28$ volts, respectively.

A series of PNP standards was prepared by pipetting 0, 0.1, 0.2, 0.3 and 0.4 ml of PNP stock solution into five 25-ml volumetric flasks. A 0.5 ml volume of PNPP solution was added to each flask. The volumetric flasks were filled to volume with pH 10.00 supporting electrolyte medium. This produced standard solutions containing 0, $3 \times 10^{-2}$, $6 \times 10^{-2}$, $9 \times 10^{-2}$, and $12 \times 10^{-2}$ mM of PNP. The PNPP concentration in each flask was $15 \times 10^{-2}$ mM. Polarographic analysis and subsequent measurements of $E_{\frac{1}{2}}$ and $I_d$ were performed as described under the DETAILED DESCRIPTION. Only one reduction wave (wave I, approximate $E_{\frac{1}{2}}$ of −0.83 volts) was observed for PNP at pH 10.00. The constant concentration of PNPP produced wave II with an approximate $E_{\frac{1}{2}}$ of −1.28 volts and a reproducible average $I_d$ value of 0.38 μA. A linear response up to a concentration of $12 \times 10^{-2}$ mM of PNP was obtained when the $I_d$ values of wave I were plotted versus PNP concentration (see Table 4 and FIG. 3).

TABLE 3

Quantitation of PNPP in the presence of $9 \times 10^{-2}$ mM PNP at pH 10.00

| Concentration ($\times 10^{-2}$ mM) | Wave I $E_{\frac{1}{2}}$ (volts)* | $I_d$ (μA)* | Wave II $E_{\frac{1}{2}}$ (volts)* | $I_d$ (μA)* |
|---|---|---|---|---|
| 0 | −0.832 | 1.63 | | |
| 15 | −0.832 | 1.81 | −1.274 | 0.44 |
| 30 | −0.825 | 1.97 | −1.292 | 0.71 |
| 45 | −0.821 | 2.24 | −1.279 | 1.00 |
| 60 | −0.819 | 2.26 | −1.276 | 1.27 |

*Each value reported represents an average of duplicate test results.

TABLE 4

Quantitation of PNP in the presence of $15 \times 10^{-2}$ mM PNPP at pH 10.00

| Concentration ($\times 10^{-2}$ mM) | Wave I $E_{\frac{1}{2}}$ (volts)* | $I_d$ (μA)* | Wave II $E_{\frac{1}{2}}$ (volts)* | $I_d$ (μA)* |
|---|---|---|---|---|
| 0 | −0.787 | 0.18 | −1.295 | 0.37 |
| 3 | −0.829 | 0.80 | −1.280 | 0.38 |
| 6 | −0.830 | 1.15 | −1.280 | 0.37 |
| 9 | −0.832 | 1.81 | −1.274 | 0.41 |
| 12 | −0.833 | 2.17 | −1.269 | 0.38 |

*Each value reported represents an average of duplicate test results.

Kinetic Determination of ALP Activity

Figure 4:
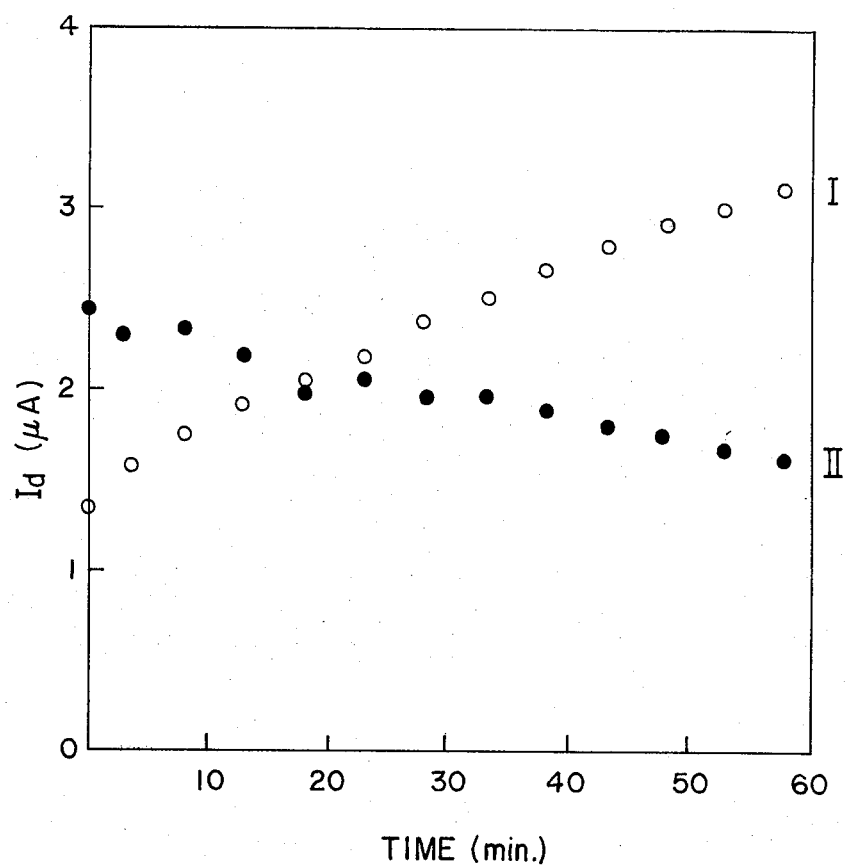
FIG. 4 contains plots of diffusion current versus time, showing the effect of alkaline phosphatase activity upon nitro group reduction waves I and II in pH 10.0 supporting electrolyte media.

A standard solution of ALP was prepared by adding 10 mg of ALP to a 10-ml volumetric flask which was filled to volume with distilled water. The ALP standard solution was mixed by gentle inversion and equilibrated in a 30° C. water bath prior to use. A stock solution of PNPP was prepared as described on page 4. A 2.0 ml volume of PNPP stock solution was pipetted into a 25-ml volumetric flask which was filled to volume with pH 10.00 supporting electrolyte medium. This produced a PNPP substrate solution containing $60 \times 10^{-2}$ mM of PNPP. The substrate was transferred to a water-jacketed polarography cell maintained at 30° C. Polarographic analysis was performed. Thereafter, 0.2 ml of the ALP standard solution was added to the contents of the polarography cell. The solution was simultaneously mixed and deaerated by purging with nitrogen gas for 3 min. Polarograms were recorded at 5-min intervals for 1 hour. The $I_d$ values of the reduction waves were measured as described on page 5. Test results have been tabulated in Table 5 and graphically depicted versus time in FIG. 4.

TABLE 5

Effect of ALP activity upon reduction waves I and II

| Time (min) | $I_d$ (μA) Wave 1 | Wave 2 |
|---|---|---|
| 0 | 1.36 | 2.46 |
| 3 | 1.60 | 2.32 |
| 8 | 1.76 | 2.36 |
| 13 | 1.94 | 2.20 |
| 18 | 2.06 | 2.02 |
| 23 | 2.20 | 2.08 |
| 28 | 2.40 | 1.96 |
| 33 | 2.52 | 1.96 |
| 38 | 2.68 | 1.90 |
| 43 | 2.82 | 1.84 |
| 48 | 2.94 | 1.76 |
| 53 | 3.04 | 1.70 |
| 58 | 3.14 | 1.64 |
| 63 | 3.30 | 1.64 |

Polarographic Behavior of PNPP and PNP in the Presence of AMP Buffers at Different pH Reagent Grade AMP was warmed to 35° C. until it was completely liquified. A total of 17.83 q of AMP was transferred to a 500-ml beaker. Two hundred ml of distilled water, 2.50 g of sodium chloride, and 0.00093 g of EDTA were added to the beaker. The resulting solution was adjusted to pH 10.00 with concentrated HCl. The AMP buffer solutions was transferred to a 250-ml volumetric flask which was filled to volume with distilled water.

Figure 5:
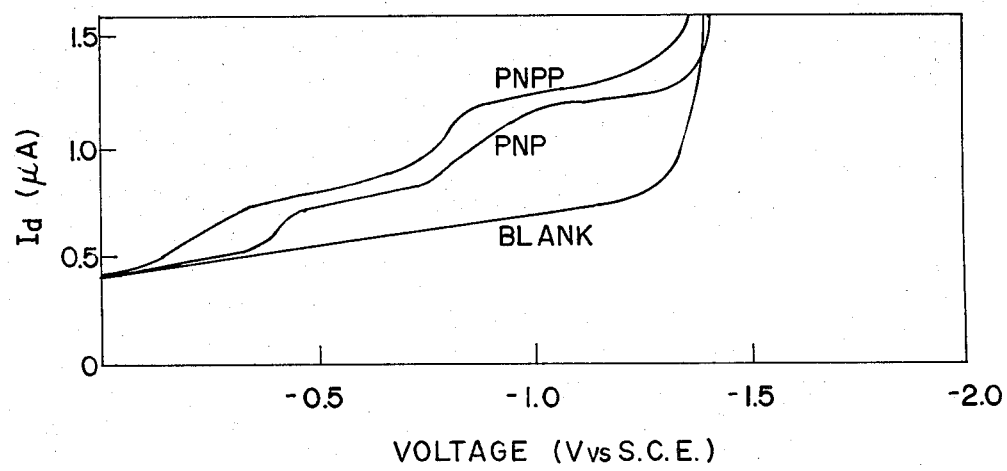
FIG. 5 contains characteristic plots of diffusion current versus voltage for an AMP buffer blank, p-nitrophenylphosphate in AMP buffer, and p-nitrophenol is AMP buffer, each at pH 12.0.

A $3 \times 10^{-2}$ mM PNPP test solution was prepared by dispensing 0.1 ml of PNPP stock solution into a 25-ml volumetric flask which was filled to volume with AMP buffer solution. The test solution was transferred to a polarography cell and deaerated. Polarographic studies were performed with a Princeton Applied Research Model 170 Electrochemistry System. Polarograms were recorded in duplicate. $E_{\frac{1}{2}}$ and $I_d$ measurements were made as described on page 5. The above procedure was similarly performed for a $3 \times 10^{-2}$ mM PNP test solution. AMP buffer solutions of pH 7.00, 8.00, 9.00, 11.00, and 12.00 were similarly prepared as described above. PNPP and PNP test solutions were prepared for each of the AMP buffer solutions. Polarographic analysis and subsequent measurement of $E_{\frac{1}{2}}$ and $I_d$ values were performed as described above. Average $E_{\frac{1}{2}}$ and $I_d$ values have been calculated from duplicate analyses of PNPP and AMP buffers of varying pH (see Table 6). Average $E_{\frac{1}{2}}$ and $I_d$ values have similarly been calculated for PNP in AMP buffers of varying pH (see Table 7). Characteristic polarograms of an AMP buffer (Blank), a PNPP test solution, and a PNP test solution, each at pH 12.00, are depicted in FIG. 5.

TABLE 6

Polarographic reduction of PNPP at AMP buffers of different pH

| pH | Wave I $E_{\frac{1}{2}}$ (volts)* | Wave I $I_d$ (μA)* | Wave II $E_{\frac{1}{2}}$ (volts)* | Wave II $I_d$ (μA)* |
|---|---|---|---|---|
| 7.00 | −0.765 | 0.189 | −1.320 | 0.106 |
| 8.00 | −0.732 | 0.183 | −1.283 | 0.136 |
| 9.00 | −0.615 | 0.142 | −1.125 | 0.154 |
| 10.00 | −0.440 | 0.100 | −0.942 | 0.154 |
| 11.00 | −0.356 | 0.073 | −0.891 | 0.150 |
| 12.00 | −0.259 | 0.067 | −0.792 | 0.146 |

*Each value reported represents an average of duplicate test results.

TABLE 7

Polarographic reduction of PNP in AMP buffers of different pH

| pH | Wave I $E_{\frac{1}{2}}$ (volts)* | Wave I $I_d$ (μA)* | Wave II $E_{\frac{1}{2}}$ (volts)* | Wave II $I_d$ (μA)* |
|---|---|---|---|---|
| 7.00 | −0.669 | 0.679 | | |
| 8.00 | −0.608 | 0.683 | | |
| 9.00 | −0.580 | 0.689 | | |
| 10.00 | −0.525 | 0.677 | | |
| 11.00 | −0.448 | 0.496 | | |
| 12.00 | −0.406 | 0.189 | −0.873 | 0.339 |

*Each value reported represents an average of duplicate test results.

Quantitation of PNPP and PNP in the Presence of AMP Buffer

Twenty-five milliliters of PNPP stock substrate solution was prepared to contain PNPP and magnesium chloride at concentrations of 225 mM and 1.5 mM, respectively. A pH 12.00 AMP buffer solution was prepared. A supporting electrolyte medium was prepared by adding 0.8 g of sodium hydroxide, 10.00 g of sodium chloride, and 0.00372 g of EDTA to a one-liter volumetric flask which was filled to volume with distilled water.

A 0.2 ml volume of PNPP stock solution, 2.7 ml of AMP buffer, and 0.1 ml of distilled water were pipetted into a test tube. The solution was mixed and the test tube was suspended in a 30° C. water bath for 15 min. A 0.5 ml aliquot was pipetted into a 50-ml volumetric flask which was filled to volume with supporting electrolyte medium. Twenty-five milliliters were transferred to a polarography cell. Polarographic analysis and subsequent $E_{\frac{1}{2}}$ and $I_d$ measurements were made. A series of four additional PNPP standard solutions were prepared by pipetting 1.0, 2.0, 3.0, and 4.0 ml of PNPP stock substrate solution into four 5-ml volumetric flasks which were filled to volume with 1.5 mM magnesium chloride solution. This produced a series of standards containing 45, 90, 135, and 180 mM of PNPP. Polarographic analysis of each test solution was performed as described above. The procedure was similarly performed in duplicate. Two reduction waves, designated as waves I and II, were observed at approximate $E_{\frac{1}{2}}$ values of −0.25 volts and −0.76 volts, respectively. The average $I_d$ values of each wave have been plotted versus PNPP concentration (see Table 8 and FIG. 6).

A 225 mM PNP stock solution was prepared by dissolving 0.78249 g of PNP in a 25-ml volumetric flask which was filled to volume with 1.5 mM magnesium chloride solution. A series of PNP standards was prepared by pipetting 0.50, 1.0, 1.5, 2.0, and 2.5 ml of PNP stock solution into each of 5-ml volumetric flasks which were filled to volume with 1.5 mM magnesium chloride solution. This produced a series of standards containing 22.5, 45.0, 67.5, 90.0 and 112.5 mM of PNP. Polarographic analysis and subsequent measurements of $E_{\frac{1}{2}}$ and $I_d$ were performed as described above. Two reduction waves, designated as wave I and II, were observed at approximate $E_{\frac{1}{2}}$ values of −0.35 volts and −0.85 volts, respectively. The average $I_d$ values of each wave have been plotted versus PNP concentration (see Table 9 and FIG. 7).

Figure 8:
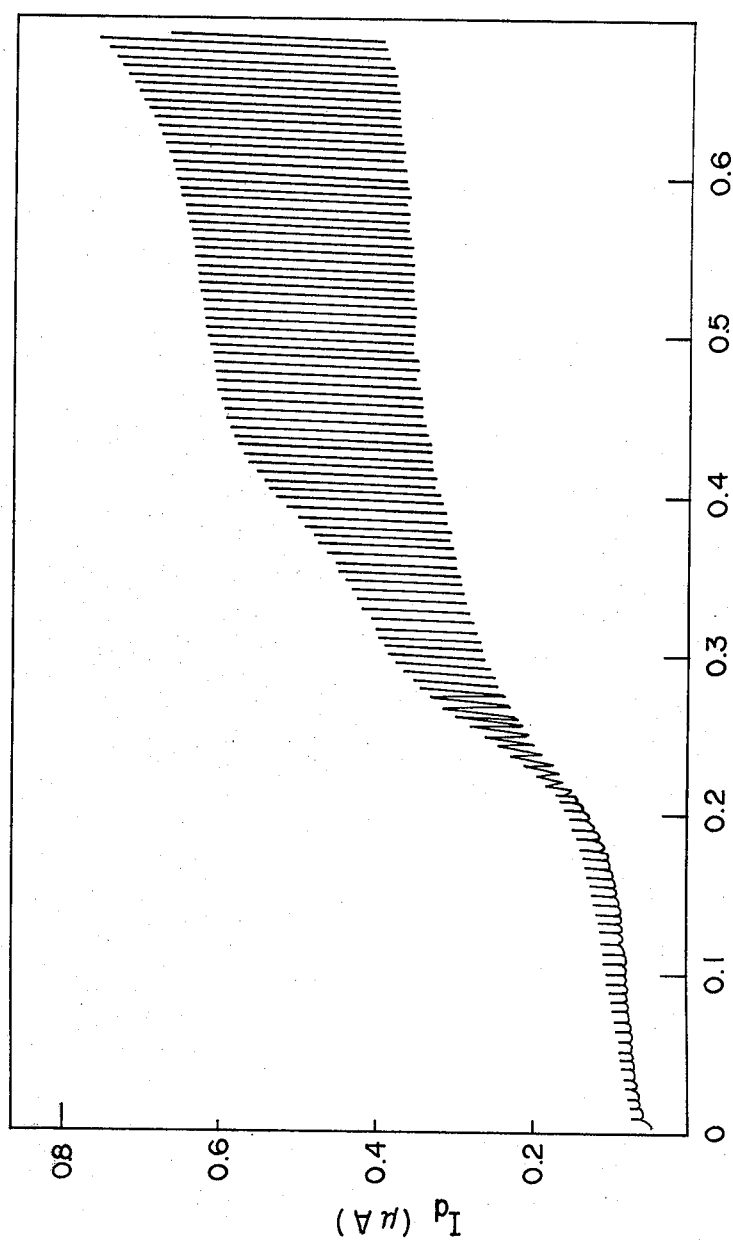
FIG. 8 is a plot of diffusion current versus voltage, showing the separation of the first reduction waves of p-nitrophenylphosphate and p-nitrophenol in AMP buffer at pH 12.0.

A standard solution containing PNPP and PNP was prepared by mixing 0.5 ml of a 90 mM PNPP standard solution with 0.5 ml of a 45 mM PNP standard. Polarographic analysis was performed as described above, however, to optimize separation of the first nitro reduction waves of PNPP and PNP, a more rapid scan rate was employed to expand the X-axis. Wave I of PNPP has been separated from wave I of PNP in the presence of AMP buffer at pH 12.00 (see FIG. 8).

TABLE 8

Quantitation of PNPP in AMP buffer of pH 12.00

| Concentration (mM) | Wave I $E_{\frac{1}{2}}$ (volts)* | Wave I $I_d$ (μA)* | Wave II $E_{\frac{1}{2}}$ (volts)* | Wave II $I_d$ (μA)* |
|---|---|---|---|---|
| 45 | −0.241 | 0.110 | −0.750 | 0.213 |
| 90 | −0.239 | 0.209 | −0.751 | 0.472 |
| 135 | −0.217 | 0.331 | −0.738 | 0.732 |
| 180 | −0.251 | 0.441 | −0.780 | 0.988 |
| 225 | −0.298 | 0.561 | −0.820 | 1.201 |

*Each value reported represents an average of duplicate test results.

TABLE 9

Quantitation of PNP in AMP buffer of pH 12.00

| Concentration (mM) | Wave I | | Wave II | |
| --- | --- | --- | --- | --- |
| | $E_{\frac{1}{2}}$ (volts)* | $I_d$ (µA)* | $E_{\frac{1}{2}}$ (volts)* | $I_d$ (µA)* |
| 22.5 | −0.366 | 0.165 | −0.901 | 0.124 |
| 45.0 | −0.350 | 0.240 | −0.849 | 0.335 |
| 67.5 | −0.344 | 0.398 | −0.858 | 0.555 |
| 90.0 | −0.343 | 0.502 | −0.848 | 0.670 |
| 112.5 | −0.311 | 0.620 | −0.830 | 0.916 |

*Each value reported represents an average of duplicate test results.

Figure 9:
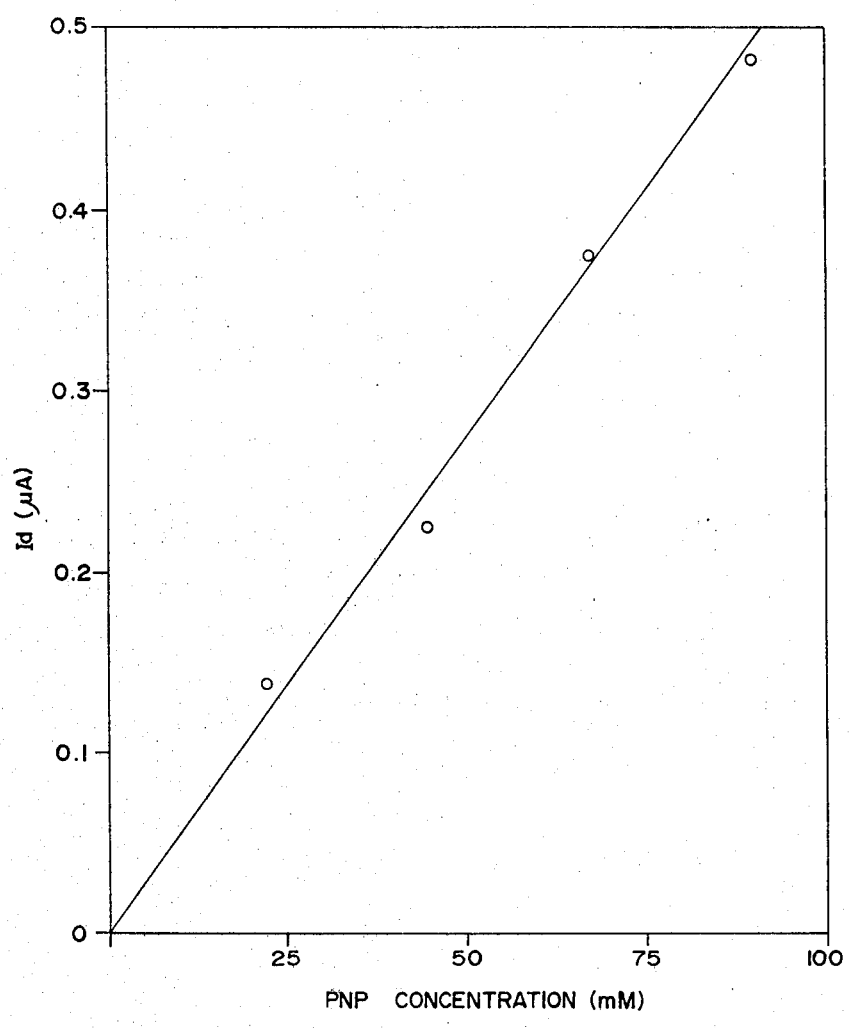
FIG. 9 is a plot of diffusion current versus p-nitrophenol concentration in the presence of 75 mM of p-nitrophenylphosphate, for nitro group reduction wave I at an $E_{\frac{1}{2}}$ value of $-0.37$ volts.

Quantitation of PNP in the Presence of AMP Buffer and a Constant Amount of PNPP Stock solutions of PNPP and PNP, each at 225 mM, were prepared as described on pages 24 and 25. A series of PNP standards was prepared by pipetting 1.0, 2.0, 3.0, and 4.0 ml of PNP stock solution into four 10-ml volumetric flasks. The volumetric flasks were filled to volume with aqueous 1.5 mM magnesium chloride solution. This produced standard solutions containing 22.5, 45.0, 67.5, and 90.0 mM of PNP with a constant PNPP concentration of 75 mM. Polarographic analysis of each standard solution was performed as described on page 19. The approximate $E_{\frac{1}{2}}$ value for reduction wave I was −0.37 volts. The $I_d$ values have been plotted versus PNP concentration (see Table 10 and FIG. 9).

TABLE 10

Quantitation of PNP in the presence of 75 mM of PNPP

| PNP Concentration (mM) | PNP reduction wave | |
| --- | --- | --- |
| | $E_{\frac{1}{2}}$ (volts) | $I_d$ (µA) |
| 22.5 | −0.334 | 0.136 |
| 45.0 | −0.362 | 0.232 |
| 67.5 | −0.366 | 0.374 |
| 90.0 | −0.406 | 0.480 |

Quantitation of PNPP in the Presence of AMP Buffer and Denatured Serum

Figure 10:
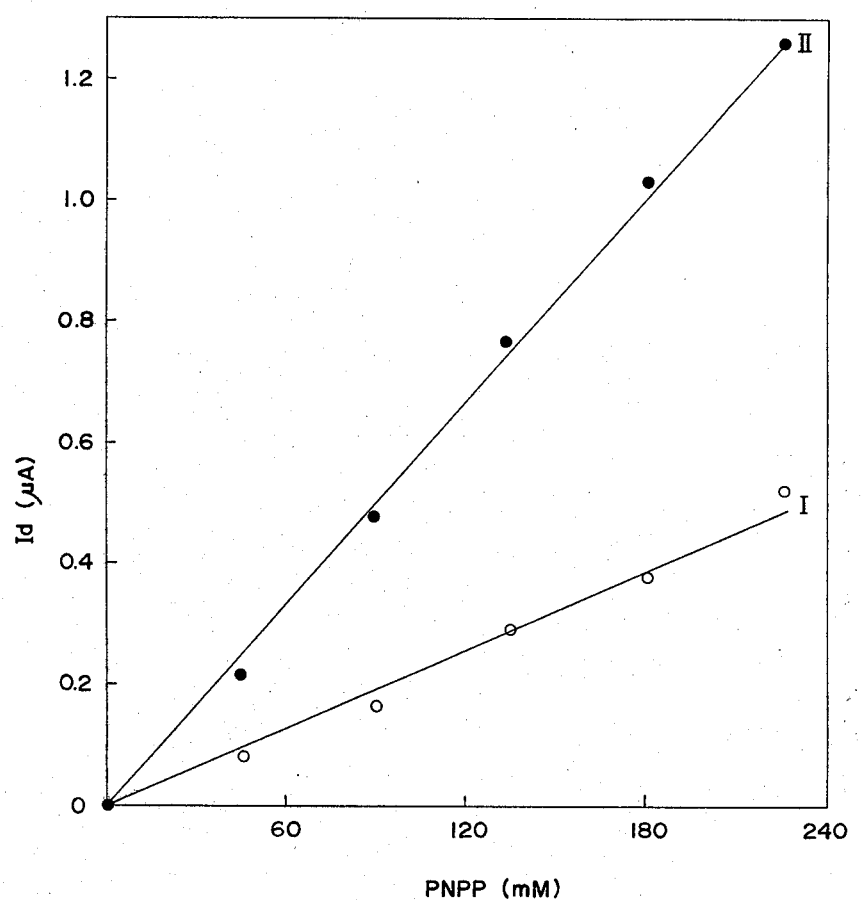
FIG. 10 contains plots of diffusion current versus p-nitrophenylphosphate concentration in the presence of denatured serum and AMP buffer at pH 12.0 for nitro group reduction waves I and II, at $E_{\frac{1}{2}}$ values of $-0.26$ and $-0.81$ volts, respectively.

Denatured serum was prepared by incubating a pooled serum at 56° C. for 2 hours. A series of PNPP standards in AMP buffer of pH 12.00 were prepared as described on page 19, however, a 0.1 ml volume of denatured pooled serum was added to each of the standards prior to being brought to volume. Polarographic analysis and subsequent $E_{\frac{1}{2}}$ and $I_d$ measurements were performed. Two reduction waves, designated as waves I and II, were observed at approximate $E_{\frac{1}{2}}$ values of −0.26 volts and −0.81 volts, respectively. The $I_d$ values for waves I and II have been plotted versus PNPP concentration (see Table 11 and FIG. 10).

TABLE 11

Polarographic reduction of PNPP in the presence of AMP buffer and denatured serum

| PNPP Concentration (mM) | Wave I | | Wave II | |
| --- | --- | --- | --- | --- |
| | $E_{\frac{1}{2}}$ (volts) | $I_d$ (µA) | $E_{\frac{1}{2}}$ (volts) | $I_d$ (µA) |
| 45 | −0.262 | 0.093 | −0.805 | 0.213 |
| 90 | −0.266 | 0.165 | −0.812 | 0.476 |
| 135 | −0.242 | 0.291 | −0.796 | 0.772 |
| 180 | −0.282 | 0.378 | −0.835 | 1.028 |
| 225 | −0.239 | 0.531 | −0.795 | 1.260 |

REFERENCES

1. Kachmar, J. F., and Moss, D. W., In fundamentals of Clinical Chemistry, Ed. by N. W. Tietz, W. B. Saunders Company, Philadelphia, London, Toronto, 2nd Ed., p. 607 (1976).
2. Ibid. pp 602–613.
3. Ibid. pp 613–618.
4. Eastham, R. D., In Biochemical Values in Clinical Medicine, John Wright and Sons Ltd., Bristol, 5th Ed., pp 146–149 (1975).
5. Ibid. pp 144–146.
6. Willard, H. H., Merritt, L. L. Jr., and Dean, J. A., In Instrumental Methods of Analysis, D. Van Nostrand Co., Toronto, London, Melbourne, 4th Ed., p 692 (1968).

We claim:

1. A process for electrochemically measuring phosphatase activity in a biological fluid sample, comprising incubating the sample with an aromaic phosphate ester reagent containing a nitro group and monitoring at electrodes arranged in the sample the current produced in incubation reaction.

2. A process according to claim 1 wherein the reagent is p-nitrophenylphosphate.

* * * * *